(12) United States Patent
Lee (10) Patent No.: US 12,156,720 B2
(45) Date of Patent: Dec. 3, 2024

(54) PORTABLE BLOOD PRESSURE MEASURING DEVICE

(71) Applicant: CHARMCARE CO., LTD., Seoul (KR)

(72) Inventor: Dong Hwa Lee, Yongin-si (KR)

(73) Assignee: CHARMCARE CO., LTD., Seoul (KR)

( * ) Notice: Subject to any disclaimer, the term of this patent is extended or adjusted under 35 U.S.C. 154(b) by 593 days.

(21) Appl. No.: 17/617,790

(22) PCT Filed: Jun. 10, 2020

(86) PCT No.: PCT/KR2020/007491
§ 371 (c)(1),
(2) Date: Dec. 9, 2021

(87) PCT Pub. No.: WO2020/251248
PCT Pub. Date: Dec. 17, 2020

(65) Prior Publication Data
US 2022/0233085 A1 Jul. 28, 2022

(30) Foreign Application Priority Data
Jun. 10, 2019 (KR) .......... 10-2019-0068003

(51) Int. Cl.
*A61B 5/022* (2006.01)
*A61B 5/00* (2006.01)

(52) U.S. Cl.
CPC .......... *A61B 5/02233* (2013.01); *A61B 5/681* (2013.01); *A61B 2562/0247* (2013.01); *A61B 2562/0261* (2013.01)

(58) Field of Classification Search
CPC ............ A61B 5/02233; A61B 5/681; A61B 2562/0247; A61B 2562/0261
See application file for complete search history.

(56) References Cited

U.S. PATENT DOCUMENTS

2018/0116534 A1* 5/2018 Tal .................. A61B 5/0205

FOREIGN PATENT DOCUMENTS

| JP | 2002541894 | 12/2002 |
|----|------------|---------|
| JP | 3873625 | 1/2007 |

(Continued)

OTHER PUBLICATIONS

International Search Report—PCT/KR2020/007491 dated Sep. 24, 2020.

*Primary Examiner* — Eric F Winakur
(74) *Attorney, Agent, or Firm* — CANTOR COLBURN LLP (57) ABSTRACT

The portable blood pressure measuring device includes a body part in which a controller for calculating blood pressure information, a display for outputting blood pressure information, and a power supply are built; a wrist strap coupled to the body part; a fastening unit for fastening the wrist strap to the wrist; a first pressure sensor coupled to a first position of the wrist strap; and a second pressure sensor coupled to a second position of the wrist strap, in which the first pressure sensor is disposed to be adjacent to a position under which the user's radial artery passes, and the second pressure sensor is disposed to be adjacent to a position under which the user's ulnar artery passes, in which the controller calculates a blood pressure based on a first pressure, a second pressure and an interference constant determined by the wrist strap.

12 Claims, 6 Drawing Sheets

(56) References Cited

FOREIGN PATENT DOCUMENTS

| JP | 2014064666 | 4/2014 |
|---|---|---|
| KR | 20090121874 | 11/2009 |
| KR | 20160014307 | 2/2016 |
| KR | 101798495 | 11/2017 |
| KR | 20180057907 | 5/2018 |
| WO | 2015177649 | 11/2015 |

\* cited by examiner

RADIAL ARTERY (1)

FIG. 6C

ULNA ARTERY (2)

FIG. 6D

RADIAL ARTERY
+ ULNA ARTERY (3)

PORTABLE BLOOD PRESSURE MEASURING DEVICE

TECHNICAL FIELD

The present disclosure relates to a portable blood pressure measuring device, and more particularly, to a portable blood pressure measuring device that measures a radial artery pressure wave and an ulnar artery pressure wave to provide a blood pressure value from which mutual interference is removed.

BACKGROUND

Recently, interest in health care has been increasing, and as the number of patients with high blood pressure and low blood pressure has been increasing, research on a wearable blood pressure measuring device that may easily check their own blood pressure has being actively conducted.

In particular, in order to improve portability of a blood pressure measuring device, a wearable blood pressure measuring device using a sensor to measure blood pressure has been developed.

In a case of measuring a pulse wave in the radial artery by using a pressure sensor, a conventional wearable blood pressure measuring device using the pressure sensor is also affected by a pulse wave generated in the ulnar artery, so that there is a problem in that a measured value thereof is inaccurate.

SUMMARY OF INVENTION

Technical Problem

The present disclosure is provided to solve the problems of the prior art described above, and an object of the present disclosure is to provide a portable blood pressure measuring device that calculates a more accurate blood pressure by disposing pressure sensors at positions corresponding to the radial artery and the ulnar artery, respectively, to measure the pressures, removing a mutual interference wavelength from the measured pressure, and using the pressures and the like.

In addition, another object of the present disclosure is to provide a portable blood pressure measuring device that may be used by being coupled to a smart watch or the like.

However, technical problems to be solved by the present embodiment are not limited to the technical problems as described above, and other technical problems may exist.

Solution to Problem

As technical means for solving the technical problems described above, according to a first aspect of the present disclosure, there is provided a portable blood pressure measuring device including: a body part in which a controller for calculating blood pressure information, a display for outputting blood pressure information, and a power supply are built; a wrist strap coupled to the body part; a fastening unit for fastening the wrist strap to the wrist; a first pressure sensor coupled to a first position of the wrist strap; and a second pressure sensor coupled to a second position of the wrist strap. The first pressure sensor is disposed to be adjacent to a position under which the user's radial artery passes, and the second pressure sensor is disposed to be adjacent to a position under which the user's ulnar artery passes. The controller calculates a blood pressure based on a first pressure and a second pressure measured by the first pressure sensor and the second pressure sensor, and an interference constant determined by the wrist strap.

Advantageous Effects

According to the above-described means for solving the problems of the present application, in a case where the portable blood pressure measuring device according to an embodiment of the present disclosure is used, the arterial pressure waves generated in the radial and ulnar arteries are respectively measured, and mutual interference is removed to measure the blood pressure with high-precision.

In addition, the portable blood pressure measuring device according to an embodiment of the present disclosure may be used by being coupled to a wearable device such as an existing smart watch or a healthcare band in addition to being used alone.

MODE OF DISCLOSURE

Hereinafter, embodiments of the present application will be described in detail with reference to the accompanying drawings so that those of ordinary skill in the art to which the present application pertains may easily implement them. However, the present application may be implemented in several different forms and is not limited to the embodiments described herein. In addition, in order to clearly explain the present application in the drawings, parts irrelevant to the description are omitted, and similar reference numerals are attached to similar parts throughout the specification.

Throughout the present specification, when a part is "connected" to another part, this includes not only a case of being "directly connected", but also a case of being "electrically connected" to another element interposed therebetween.

Throughout the present specification, when a member is said to be located "on" another member, this includes not only a case where a member is in contact with another member but also a case where another member is present between the two members.

Throughout the present specification, a 'wrist' is a body part located between a hand and an arm, and may include a 'wrist' located between the wrist and the elbow.

Hereinafter, an embodiment of the present disclosure will be described in detail with reference to the accompanying drawings.

Figure 1:
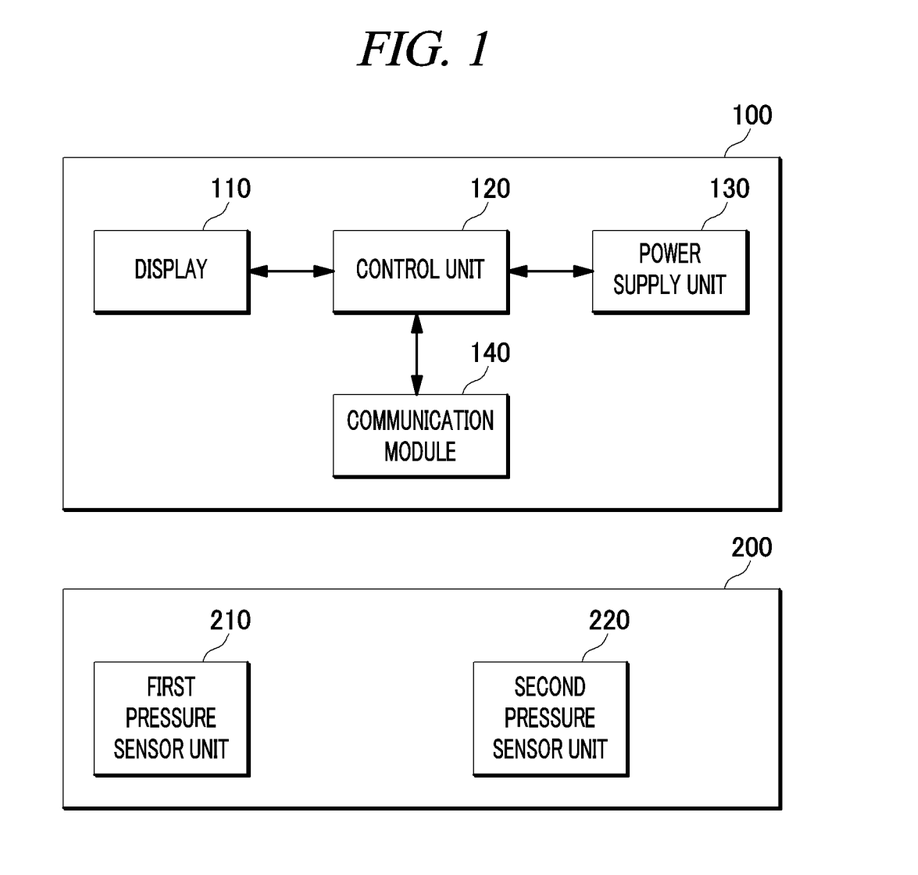
FIG. 1 is a block diagram illustrating a configuration of a portable blood pressure measuring device according to an embodiment of the present disclosure.

FIG. 1 is a block diagram illustrating a configuration of a portable blood pressure measuring device according to an embodiment of the present disclosure.

As illustrated in the drawing, the portable blood pressure measuring device includes a body part 100 and a sensor 200. The body part 100 includes a display 110, a controller 120, and a power supply 130, and may further include a communication module 140. The sensor 200 may include a first pressure sensor 210 and a second pressure sensor 220.

The display 110 may be implemented with various types of display modules, such as a liquid crystal display, a reflective display, and an OLED display. The display 110 may display a blood pressure calculated by the controller 120 or other information.

The controller 120 may calculate an arterial blood pressure based on the pressures measured by the first pressure sensor 210 and the second pressure sensor 220. An arterial blood pressure $P_a$ is calculated by Equation 1 below.

$$S_a = P_a + P_v * K$$
$$S_v = P_v + P_a * K$$
$$P_a = S_a - S_v * K + P_a * K^2$$
$$P_a = \frac{S_a - S_v * K}{1 - K^2}$$

[Equation 1]

In Equation 1, $P_a$ is a blood pressure of the radial artery, Pv is a blood pressure of the ulnar artery, $S_a$ is a blood pressure value measured by the first pressure sensor 210, $S_v$ is a blood pressure value measured by the second pressure sensor 220, and K is an interference constant determined by the wrist strap.

In a case where the first pressure sensor 210 measures the blood pressure, not only the blood pressure $P_a$ of the radial artery but also the blood pressure Pv of the ulnar artery is transmitted through the wrist strap 500 and the pressing unit 300 surrounding the wrist. At this time, when the interference constant is defined as K, the first pressure sensor 210 measures the blood pressure by adding the value of the blood pressure Pv of the ulnar artery multiplied by the interference constant K to the blood pressure $P_a$ of the radial artery. On the contrary, the second pressure sensor 220 measures the blood pressure by adding the value of the blood pressure $P_a$ of the radial artery multiplied by the interference constant K to the blood pressure Pv of the ulnar artery. If this is arranged according to Equation 1, the actual blood pressure $P_a$ of the radial artery may be calculated.

The controller 120 controls the sensor 200 to measure the blood pressure when the blood pressure measurement is required, such as when blood pressure measurement request information is received or the blood pressure measurement is automatically set at regular intervals, and displays the measured information on the display 110.

For example, the controller 120 may perform a series of processes in which the blood pressure may be measured in time unit, the measured blood pressure information may be displayed on the display 110, an alarm may be generated in a case where a blood pressure outside a preset range is measured, and the corresponding information may be transmitted to a preset mobile phone or medical facility by using the communication module 140.

The power supply 130 may be configured as a built-in type in the body part 100 or may be configured as an exchangeable replacing-type battery.

The communication module 140 may transmit and receive data such as blood pressure information measured by communication between the body part 100 and various external devices (servers or terminals) in a set communication format. In addition, the communication module 140 may receive update information such as a program related to the blood pressure measurement, from an external device and transmit the information to the controller 120.

The sensor 200 for measuring the blood pressure may include the first pressure sensor 210 and the second pressure sensor 220.

The first pressure sensor 210 and the second pressure sensor 220 included in the sensor 200 are adjacent to positions under which the radial artery A and the ulnar artery B pass, respectively, and are disposed to be in close contact with the wrist.

At this time, the first pressure sensor 210 and the second pressure sensor 220 may be a strain gauge-based semiconductor thin film sensor, a capacitive thin film sensor for detecting a capacity change according to a pressure, a piezoresistive sensor using a piezo resistance effect, or other various pressure sensors.

Here, the strain gauge-based semiconductor thin film sensor has an advantage that only the resistance change is controlled by arranging four resistors on a diaphragm in a Wheatstone bridge form. The capacitive thin film sensor has advantages that it has strong heat resistance and corrosion resistance, and high-precision measurement is possible when measuring the pressure. The piezoresistive sensor has advantages that high sensitivity, excellent linearity, and reproducibility are excellent when measuring the pressure, and it is easy to mass-produce.

In addition, the first pressure sensor 210 and the second pressure sensor 220 may each include a plurality of sensors arranged in an array form.

Since the first pressure sensor 210 and the second pressure sensor 220 each measure pressure using the plurality of sensors, at least one of a maximum value, a minimum value, a maximum frequency value, and an average value among the pressures sensed by the sensors included in each of the pressure sensors 210 and 220, when the blood pressure is calculated, may be used by being specified as the first pressure and the second pressure, respectively.

Figure 2:
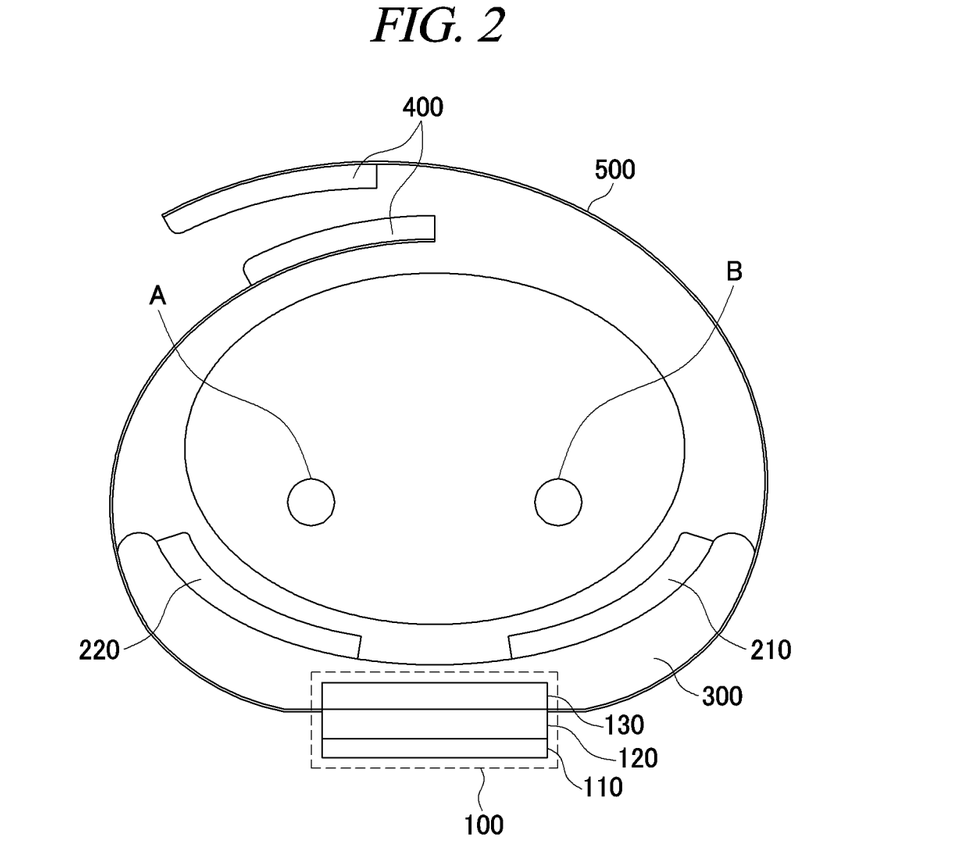
FIG. 2 is a sectional view illustrating a configuration of a portable blood pressure measuring device according to an embodiment of the present disclosure.

FIG. 2 is a sectional view illustrating a configuration of a portable blood pressure measuring device according to an embodiment of the present disclosure.

In the portable blood pressure measuring device, the body part 100, the first pressure sensor 210, the second pressure sensor 220, the pressing unit 300, and the fastening unit 400 may be located on the wrist strap 500.

In the body part 100, the display 110 is located outside the body part 100 furthest from the wrist when being worn on the wrist so that the user may easily recognize the display 110. The controller 120 and the power supply 130 are located inside the display 110 and are not limited to a specific position.

The first pressure sensor 210 is disposed adjacent to a position under which the user's radial artery A passes, on the wrist strap 500, and the second pressure sensor 220 is disposed adjacent to a position under which the user's ulnar artery B passes, on the wrist strap 500.

The body part 100 may be located below the first pressure sensor 210 and the second pressure sensor 220, and may be electrically connected to the first pressure sensor 210 and the second pressure sensor 220.

The pressing unit 300 may be disposed between the first pressure sensor 210 and the second pressure sensor 220, and the wrist strap 500 to adjust a degree of contact between the first pressure sensor 210 and the second pressure sensor 220, and the wrist. The pressing unit 300 may be an air bag, an actuator, a thermal expansion device, a deformable alloy device, or the like.

The air bag may be operated by receiving air supplied by a valve or the like so that the sensor 200 is in close contact with the wrist, and the actuator may be operated by using electricity, hydraulic pressure, compressed air, or the like so that the sensor 200 is in close contact with the wrist. The degree of contact of the wrist strap 500 and the sensor 200 may be adjusted by using the thermal expansion device having a large coefficient of thermal expansion or using the deformable alloy device.

The fastening units 400 are located at both ends of the wrist strap 500 to fasten one end and the other end of the wrist strap 500, and the degree of contact of the wrist strap 500 may be adjusted in consideration of the thickness of the wrist. In the configuration of FIG. 2, respective pressure sensors are located adjacent to the radial artery A and the ulnar artery B, and the body part 100 is located at the lower portion thereof, so the body part 100 is located opposite to the back of the user's hand.

Figure 3:
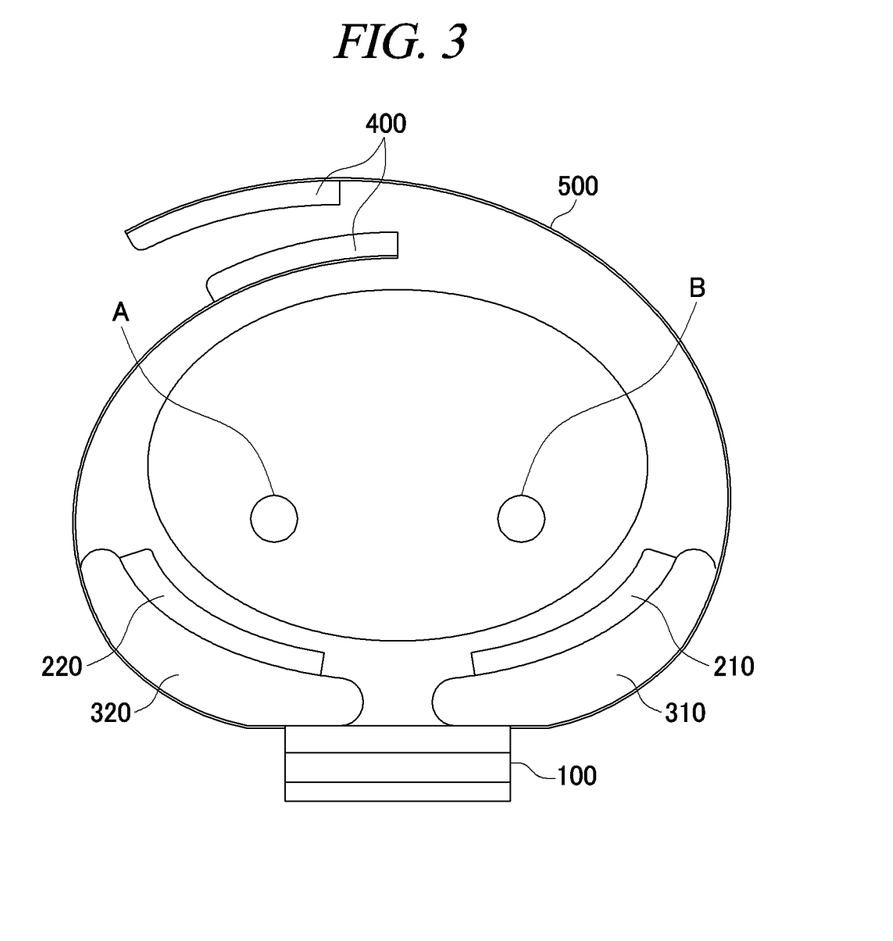
FIG. 3 is a sectional view for explaining a portable blood pressure measuring device having a pressing unit for each pressure sensor according to an embodiment of the present disclosure.

FIG. 3 is a sectional view illustrating a portable blood pressure measuring device having a pressing unit for each pressure sensor according to an embodiment of the present disclosure.

Instead of the pressing unit 300 illustrated in FIG. 2, a first air bag 310 and a second air bag 320 may be installed between the wrist strap 500 and the wrist to serve as the pressing unit. The first air bag may be disposed between the wrist strap 500 and the first pressure sensor 210 disposed adjacent to the position under which the radial artery A passes, and the second air bag 320 may be disposed between the wrist strap 500 and second pressure sensor 220 disposed adjacent to the position under which the ulnar artery B passes.

Figure 4:
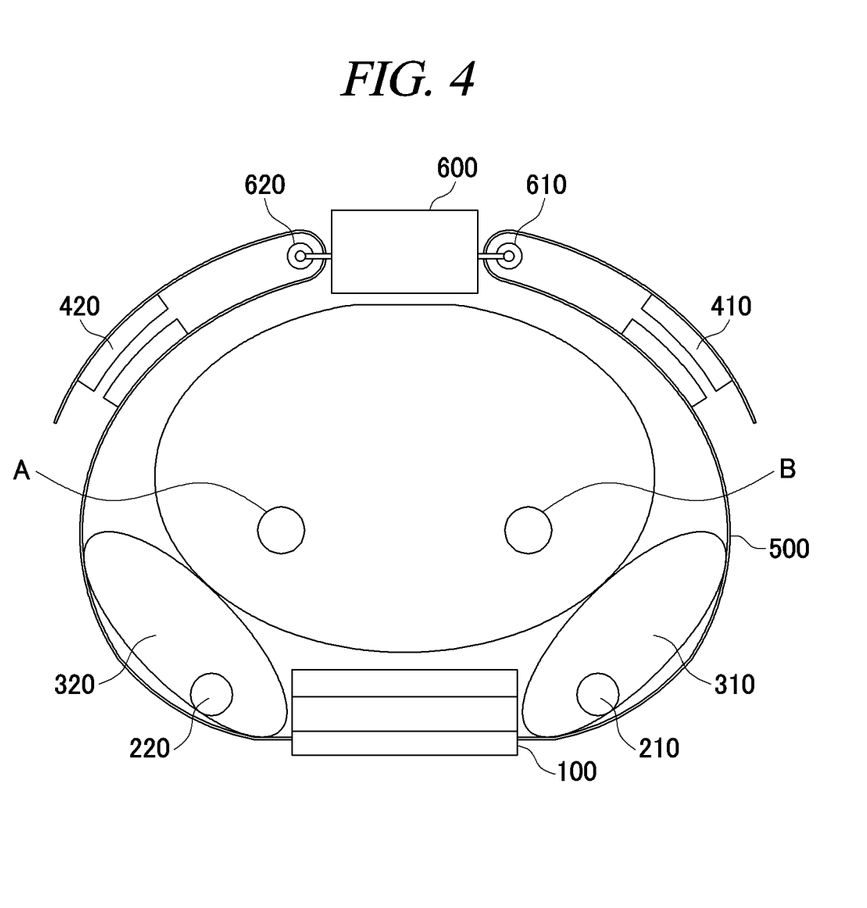
FIG. 4 is a sectional view illustrating a portable blood pressure measuring device used by being coupled to a smart watch or the like according to an embodiment of the present disclosure.

FIG. 4 is a sectional view illustrating a portable blood pressure measuring device used by being coupled to a smart watch or the like according to an embodiment of the present disclosure.

The portable blood pressure measuring device may be used by being coupled to a smart watch module 600. Both ends of the wrist strap 500 may have first fastening means 410 and second fastening means 420 coupled to the smart watch module 600 so as to couple to a first connection portion 610 and a second connection portion 620 of the smart watch module 600. A length of the wrist strap 500 may be adjusted by using the first fastening means 410 and the second fastening means 420 to adjust the degree of contact with the wrist.

In order to fasten the smart watch module 600 to the wrist strap 500, a separate device including the first connection portion 610 and the second connection portion 620 may be coupled or a smart watch case including a connection portion may be used, but a method of coupling the smart watch module 600 is not limited thereto.

The first pressure sensor 210 may include the first air bag 310 and the first pressure sensor provided in the first air bag 310, and the second pressure sensor 220 may include the second air bag 320 and a second pressure sensor provided in the second air bag 320.

Figure 5:
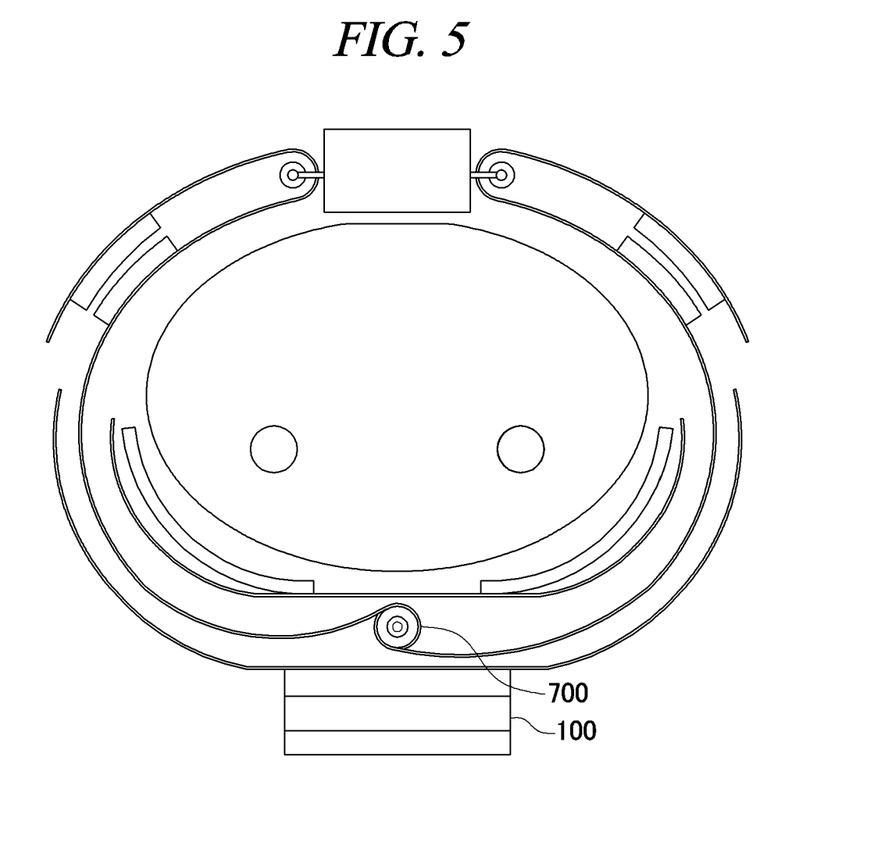
FIG. 5 is a sectional view illustrating a portable blood pressure measuring device using a roller instead of the pressing unit according to an embodiment of the present disclosure.

FIG. 5 is a sectional view illustrating a portable blood pressure measuring device using a roller instead of a pressing unit according to an embodiment of the present disclosure.

In the portable blood pressure measuring device, a wrist strap 500 including a roller 700 instead of the pressing unit 300 may be used. When the roller 700 rotates, the length of the wrist strap 500 is adjusted, so that when the blood pressure is measured, the roller may be rotated to tighten the wrist strap 500 to be in close contact with the wrist.

FIG. 6 is a diagram illustrating the ulnar artery pressure waves and the radial artery pressure waves measured according to an embodiment of the present disclosure. That is, FIG. 6A is a diagram for explaining systolic and diastolic blood pressure, FIG. 6B is a diagram illustrating a blood pressure waveform generated in the radial artery, FIG. 6C is a diagram illustrating a blood pressure waveform generated in the ulnar artery, and FIG. 6D is a diagram illustrating results of measuring the radial artery waveform and the ulnar artery waveform together.

Figure 6A:
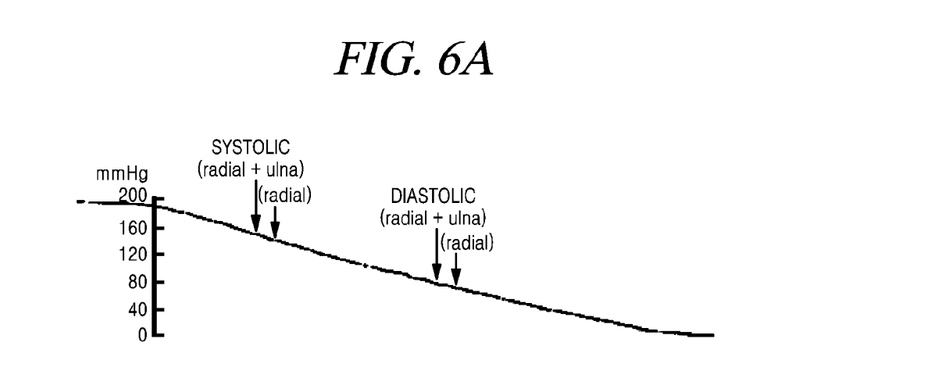
FIGS. 6A, 6B, 6C, and 6D are diagrams illustrating ulnar artery pressure waves and radial artery pressure waves measured according to an embodiment of the present disclosure.
Figure 6B:
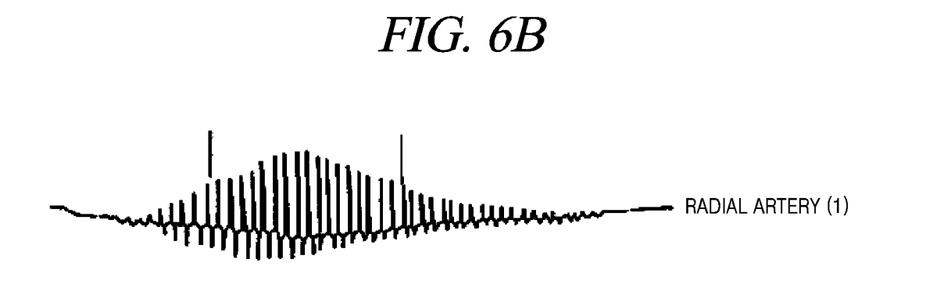
Figure 6C:
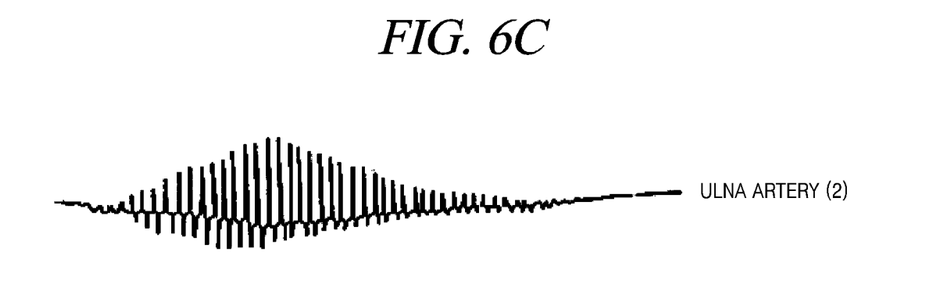
Figure 6D:
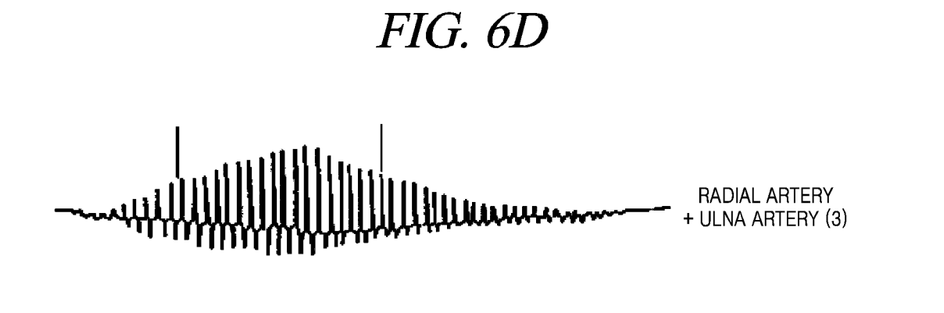

In a case where the blood pressure is measured by using the sensor 200 in the portable blood pressure measuring device, an arterial pressure wave is amplified by a mutual interference signal between the radial and ulnar arterial pressure waves transmitted by a cuff strip surrounding the wrist, and the amplified blood pressure may be measured as illustrated in FIG. 6d. In the present disclosure, since the blood pressure is measured at two places of the first pressure sensor 210 and the second pressure sensor 220, even if the signal of FIG. 6d is measured in the first pressure sensor 210, the waveform of FIG. 6c may be removed in consideration of the measured value in the second pressure sensor 220 and the interference constant, and the blood pressure may be measured based on the waveform of FIG. 6b. In this case, SYSTOLIC is the systolic blood pressure, and DIASTOLIC is the diastolic blood pressure.

An embodiment of the present disclosure may also be implemented in a form of a recording medium including instructions executable by a computer, such as a program module executed by a computer. Computer-readable media may be any available media that may be accessed by a computer and includes both volatile and nonvolatile media, removable and non-removable media. In addition, the computer-readable media may include computer storage media. Computer storage media includes both volatile and nonvolatile, removable and non-removable media implemented in any method or technology for storage of information such as computer readable instructions, data structures, program modules, or other data.

Although the method and the system of the present disclosure have been described with reference to specific embodiments, some or all of their configuration elements or operations may be implemented by using a computer system having a general purpose hardware architecture.

The foregoing description of the present application is for illustration, and those of ordinary skill in the art to which the present application pertains will understand that it may be easily modified into other specific forms without changing the technical spirit or essential features of the present application. Therefore, it should be understood that the embodiments described above are illustrative in all respects and not restrictive. For example, each configuration element described as a single type may be implemented in a dispersed form, and likewise configuration elements described as distributed may be implemented in a combined form.

The scope of the present application is indicated by the following claims rather than the above detailed description, and all changes or modifications derived from the meaning and scope of the claims and their equivalents should be construed as being included in the scope of the present application.

10: blood pressure measuring device
100: body part, 110: display
120: controller, 130: power supply
140: communication module
200: sensor
210: first pressure sensor, 220: second pressure sensor
300: pressing unit
310: first air bag, 320: second air bag
400: fastening unit
410: first fastening means, 420: second fastening means
500: wrist strap
600: smart watch module
610: first connection portion, 620: second connection portion
700: roller

The invention claimed is:

1. A portable blood pressure measuring device comprising:
    a body part in which a controller for calculating blood pressure information is built;
    a wrist strap coupled to the body part;
    a first pressure sensor coupled to a first position of the wrist strap; and
    a second pressure sensor coupled to a second position of the wrist strap,
    wherein the first pressure sensor is disposed to be adjacent to a position under which the user's radial artery passes, and the second pressure sensor is disposed to be adjacent to a position under which the user's ulnar artery passes, and
    wherein the controller calculates a blood pressure based on a first pressure and a second pressure measured by the first pressure sensor and the second pressure sensor, and an interference constant determined by the wrist strap.

2. The portable blood pressure measuring device of claim 1, further comprising:
    a fastening unit for fastening the wrist strap to the wrist.

3. The portable blood pressure measuring device of claim 1, wherein the controller calculates the blood pressure according to Equation 1 below, $$P_a = \frac{S_a - S_v * K^*}{1 - K^2} \quad \text{[Equation 1]}$$

$P_a$: calculated blood pressure,
$S_a$: blood pressure value measured by first pressure sensor,
$S_v$: blood pressure value measured by second pressure sensor,
K: interference constant determined by wrist strap.

4. The portable blood pressure measuring device of claim 1, wherein the body part is located below the first pressure sensor and the second pressure sensor, and is electrically connected to the first pressure sensor and the second pressure sensor.

5. The portable blood pressure measuring device of claim 1, wherein both ends of the wrist strap are coupled to first fastening means and second fastening means coupled to a smart watch module that is distinct from the body part.

6. The portable blood pressure measuring device of claim 1, wherein the first pressure sensor and the second pressure sensor are a strain gauge-based semiconductor thin film sensor, a capacitive thin film sensor for detecting a capacity change according to a pressure, or a piezoresistive sensor using a piezo resistance effect.

7. The portable blood pressure measuring device of claim 1, further comprising:
    a pressing unit disposed between the first pressure sensor and the second pressure sensor, and the wrist strap,
    wherein a degree of contact between the first pressure sensor and the second pressure sensor, and the wrist is adjusted by the pressing unit.

8. The portable blood pressure measuring device of claim 7, wherein the pressing unit is an air bag, an actuator, a thermal expansion device, or a deformable alloy device.

9. The portable blood pressure measuring device of claim 1, wherein the first pressure sensor includes a first air bag and a first pressure sensor provided in the first air bag,
    wherein the second pressure sensor includes a second air bag and a second pressure sensor provided in the second air bag, and
    wherein the pressure sensed by the first pressure sensor is used as the first pressure, and the pressure sensed by the second pressure sensor is used as the second pressure.

10. The portable blood pressure measuring device of claim 1, wherein the first pressure sensor and the second pressure sensor each include a plurality of sensors disposed in an array, and
    wherein the controller specifies a maximum value, a minimum value, a maximum frequency value, or an average value, as the first pressure, among the pressures sensed by the sensors included in the first pressure sensor, and specifies a maximum value, a minimum value, a maximum frequency value, or an average value, as the second pressure, among the pressures sensed by the sensors included in the second pressure sensor.

11. The portable blood pressure measuring device of claim 1, further comprising:
    a communication module for performing data communication,
    wherein the controller transmits the measured blood pressure information to an external device through the communication module.

12. The portable blood pressure measuring device of claim 1, wherein the body part further includes a display for outputting the blood pressure information and a power supply.

* * * * *